United States Patent
Pham et al.

[11] Patent Number: 6,156,944
[45] Date of Patent: Dec. 5, 2000

[54] EXTRACTION OF HYDROGEN FLUORIDE FROM A HALOCARBON/HYDROGEN FLUORIDE AZEOTROPIC MIXTURE

[75] Inventors: Hang T. Pham, Amherst; Rajiv R. Singh, Getzille; Charles F. Swain, Williamsville; Michael Van Der Puy, Amherst, all of N.Y.

[73] Assignee: Honeywell International Inc., Morristown, N.J.

[21] Appl. No.: 09/034,104

[22] Filed: Mar. 3, 1998

Related U.S. Application Data

[63] Continuation-in-part of application No. 08/675,021, Jul. 3, 1996, abandoned.

[51] Int. Cl.$^7$ .................................................. C07C 17/38
[52] U.S. Cl. ............................................ 570/177; 570/180
[58] Field of Search ..................................... 570/180, 177

[56] References Cited

U.S. PATENT DOCUMENTS

| | | | |
|---|---|---|---|
| 3,873,629 | 3/1975 | Jones | 260/653 |
| 3,947,558 | 3/1976 | Van Eijl | 423/483 |
| 5,414,165 | 5/1995 | Nappa et al. | 570/169 |
| 5,461,177 | 10/1995 | Manzer et al. | 570/178 |
| 5,523,015 | 6/1996 | Tsuda et al. | 203/50 |

FOREIGN PATENT DOCUMENTS

| | | |
|---|---|---|
| 684687 | 4/1964 | Canada . |
| 0 472 391 A1 | 2/1992 | European Pat. Off. . |
| 0 583 551 A1 | 2/1994 | European Pat. Off. . |
| 1567494 | 8/1962 | Germany . |
| WO 95/04022 | 2/1995 | WIPO . |

*Primary Examiner*—Alan Siegel
*Attorney, Agent, or Firm*—Synnestvedt & Lechner LLP

[57] ABSTRACT

A process for the separation of mixtures containing halocarbons and hydrogen fluoride. Either water alone or a blend comprising water and hydrogen fluoride is added to a mixture comprising a halocarbon and hydrogen fluoride to thereby form a first phase rich in the halocarbon and a second phase rich in hydrogen fluoride and water. The most preferred halocarbon is 1,1,1,3,3-pentafluoropropane. Preferably, the first and second phases are then separated. Optionally, the second phase rich in hydroger fluoride and water is also separated.

20 Claims, No Drawings

EXTRACTION OF HYDROGEN FLUORIDE FROM A HALOCARBON/HYDROGEN FLUORIDE AZEOTROPIC MIXTURE

CROSS-REFERENCE TO RELATED APPLICATION

This is a continuation-in-part of application Ser. No. 08/675,021 filed on Jul. 3, 1996, now abandoned.

BACKGROUND OF THE INVENTION

1. Field of the Invention

The present invention pertains to a process for the separation of a halocarbon and hydrogen fluoride from a mixture of the halocarbon and hydrogen fluoride. More particularly, the invention relates to the separation of azeotropic mixtures of halocarbons and hydrogen fluoride.

2. Description of the Prior Art

It is well known in the art to react hydrogen fluoride with various compounds in order to produce fluorinated halocarbons or fluorocarbons. Such materials are useful as solvents, refrigerants, blowing agents and aerosol propellants, among other uses. Hydrofluorocarbons (HFC's) are a preferred class of halocarbons because they are considered to be much more environmentally advantageous than halocarbons such as hydrochlorofluorocarbons (HCFC's) or chlorofluorocarbons (CFC's) for the reason that they are essentially non-ozone depleting, non-flammable, and non-toxic as compared to chlorine-containing chlorocarbons. In the production of fluorocarbons and HFC's, a typical product stream contains unreacted hydrogen fluoride, other starting reagents, and by-products as well as the desired product. Various conventional separation techniques, for example, distillation and scrubbing, may be used to separate certain by-products and starting materials from a product stream; however, particular difficulty can be experienced in removing halocarbons, including hydrofluorocarbons from hydrogen fluoride. This is especially true for those HFC's having boiling points close to that of HF. In a typical method of preparing hydrofluorocarbons, precursor reagents are fluorinated with hydrogen fluoride. It would be desirable to produce substantially pure hydrofluorocarbons; however, this has proved to be difficult since many hydrofluorocarbons, especially hydrofluorocarbons having three or move carbon atoms, and hydrogen fluoride form azeotropic mixtures which are substantially inseparable by distillation.

The prior art has suggested various methods of separating azeotropic mixtures of hydrofluorocarbons. In this regard, European patent application bearing Publication No. EP 0 472 391 suggests separating HFC-134a from a mixture containing HFC-134a and chlorine-containing HCFC's using an extraction agent such as trichloroethylene or perchloroethylene. European patent application bearing Publication No. EP 0 467 531 teaches a method of separating HFC-134a from a mixture of HFC-134a and HF by passing the mixture through a distillation column to form a residue of pure HFC-134a and then collecting the residue. European patent application bearing Publication No. EP 0 583 551 uses HF to extract a relatively small amount of HF from an HFC-134a/HF azeotrope. HFC-134a is a two carbon fluorocarbon. U.S. Pat. No. 5,211,817 attempts a separation of fluorocarbons from azeotropic mixtures containing HF by column distillation and withdrawing a vapor sidestream followed by introducing the sidestream into a rectifying column equipped with a condenser and operated at a high reflux ratio. Sulfuric acid has been used heretofore to separate a gaseous mixture of HF from a chlorine-containing chlorofluorocarbon, namely FC-22, as described in U.S. Pat. No. 3,873,629. And U.S. Pat. No. 3,947,558 discloses the recovery of HF from $C_1$–$C_3$ halocarbons using a monoglycol. The methods of separation described in the aforementioned publications provide less than satisfactory solutions to the problem.

According to the preferred form of the present invention, there is provided a method for separating a hydrofluorocarbon and hydrogen fluoride from a mixture of the hydrofluorocarbon and hydrogen fluoride by using either water alone or a water/HF mixture as an extracting agent. Although water/HF azeotropic compositions are well known, their use as an extracting agent for the separation of HF from halocarbons such as those which contain three or more carbon atoms is not known. In addition, the use of water as an HF extracting agent for halocarbon is not known.

SUMMARY OF THE INVENTION

The invention provides a process for separating a halocarbon and hydrogen fluoride from a mixture containing a halocarbon and hydrogen fluoride which comprises adding a blend comprising water and hydrogen fluoride to a mixture comprising a halocarbon and hydrogen fluoride to thereby form a first phase rich in the halocarbon and a second phase rich in hydrogen fluoride and water, wherein the weight ratio of water to hydrogen fluoride in the added blend ranges from about 2:3 to about 4:1 and wherein the weight ratio of water to hydrogen fluoride in the formed second phase ranges from about 1:3 to about 1:1.

In one embodiment of the present invention, there is provided a process for separating by extraction a hydrofluorocarbon and hydrogen fluoride from an azeotropic mixture comprising a hydrofluorocarbon containing at least three carbon atoms and at least about 25 wt. % of hydrogen fluoride which comprises adding a blend comprising water and hydrogen fluoride to said azeotropic mixture to thereby form a first phase rich in the hydrofluorocarbon and containing nc greater than about 1 wt. % of HF and a second phase rich in hydrogen fluoride and water, wherein the weight ratio of water to hydrogen fluoride in the added blend ranges from about 2:3 to about 4:1 and wherein the weight ratio of water to hydrogen fluoride in the formed second phase ranges from about 1:3 to about 1:1.

The invention also provides a process for separating a halocarbon and hydrogen fluoride from a mixture containing a halocarbon and hydrogen fluoride which comprises adding water alone to a mixture comprising a halocarbon and hydrogen fluoride to thereby form a first phase rich in the halocarbon and a second phase rich in hydrogen fluoride and water, wherein the weight ratio of added water to hydrogen fluoride ranges from about 3:2 to about 1:5 and wherein the weight ratio of water to hydrogen fluoride in the formed second phase ranges from about 3:2 to about 1:5.

In another embodiment of the present invention, there is provided a process for separating by extraction a hydrofluorocarbon and hydrogen fluoride from an azeotropic mixture comprising a hydrofluorocarbon containing at least three carbon atoms and at least about 25 wt. % of hydrogen fluoride which comprises adding neutral water to said azeotropic mixture to thereby form a first phase rich in the hydrofluorocarbon and containing no greater than about 1 wt. % of HF and a second phase rich in hydrogen fluoride and water, wherein the weight ratio of added water to hydrogen fluoride ranges from about 3:2 to about 1:5 and wherein the weight ratio of water to hydrogen fluoride in the formed second phase ranges from about 3:2 to about 1:5.

DETAILED DESCRIPTION OF THE INVENTION

In the process of the instant invention, one commences with a mixture comprising a halocarbon and hydrogen fluoride. The mixture may be an azeotrope, but this condition is not necessary. In the preferred embodiment, the halocarbon is a hydrofluorocarbon which has three or more carbon atoms, and most preferably three or four carbon atoms. As used in this invention, the term "hydrofluorocarbon" means compounds which include atoms of carbon, hydrogen and fluorine, but not other halogen atoms. The HFC may be, for example pentafluoropropane, such as 1,1,1,3,3-pentafluoropropane which is also known as HFC-245fa or 1,1,2,3,3-pentafluoropropane which is also known as HFC-245ea. HFC-245fa is itself well known in the art, as described in U.S. Pat. No. 2,942,036; Canadian Patent No. 684,687; EP 381 986A; JP 02,272,086 and WO 95/04022. The disclosures of all of the foregoing patent publications are incorporated herein by reference. The process is also particularly useful for separating hydrogen fluoride from 1,1,1,2,2,5-hexafluoro-butane, which is also known as HFC-356 mcfq.

In one exemplary embodiment of the invention, one begins with a mixture of the liquid or gaseous HFC and at least about 25 wt. % hydrogen fluoride and then adds a blend of water and hydrogen fluoride to the mixture. The amount of hydrogen fluoride in the mixture can be relatively high, for example, about 30 to about 70 wt. % hydrogen fluoride. In this embodiment for separating the HFC and hydrogen fluoride from the mixture containing the HFC and hydrogen fluoride, a blend comprising water and hydrogen fluoride is added to the mixture comprising the HFC and hydrogen fluoride to form a first phase rich in the hydrofluorocarbon and a second phase rich in hydrogen fluoride and water. The blend of water and hydrogen fluoride is preferably an azeotropic blend and more preferably a binary azeotrope. Upon the addition of the water/HF blend to the HFC/HF mixture, the hydrogen fluoride is concentrated in a second phase, that is, hydrogen fluoride from the HFC/hydrogen fluoride mixture leaves the mixture and becomes more concentrated in the HF/water. In effect the HF/water blend is a stronger azeotrope than the HFC/hydrogen fluoride mixture. This is exemplified by the extent to which the HF is depleted from the HFC/hydrogen fluoride mixture. For example, and depending on various factors such as the particular HFC involved and the concentration of the HF in the mixture, the HFC-rich phase can contain as little as about 1 wt. % HF or less, for example, preferably no greater than about 0.5 wt. %, and more preferably no greater than about 0.1 wt. %. The use of multiple extractions can reduce the HF concentration to effectively about 0 wt. %.

The amount of HF/water blend needed for the separation depends on the amount of HF present in the system. In the preferred embodiment, the weight ratio of water to hydrogen fluoride in the blend ranges from about 2:3 to about 4:1. More preferably the weight ratio ranges from about 2:3 to about 2:1 and most preferably from about 2:3 to about 1:1.

Preferably, the extraction is conducted at a temperature of from about 0° C. to about 100° C., more preferably from about 0° C. to about 40° C., and most preferably from about 20° C. to about 40° C. The extraction is usually conducted at normal atmospheric pressure; however, higher or lower pressure conditions may be used by those skilled in the art. Upon adding the HF/water blend to the mixture of HFC and HF, two phases rapidly form. A first phase is formed which is rich in the fluorocarbon and a second phase which is rich in HF/water. By the term "rich" is meant, the phase contains more than 50% of the indicated component in that phase, and preferably more than 80% of the indicated component in that phase. In the preferred embodiment, the weight ratio of water to hydrogen fluoride in the resulting second phase ranges from about 1:3 to about 1:1, preferably from about 1:3 to about 2:3, and most preferably from about 1:3 to about 3:7.

After the separation of the phases, one removes the phase rich in the HFC from the phase rich in the hydrogen fluoride and water. This may be done by decanting, siphoning, distillation or other techniques well known in the art. One may optionally repeat the HFC extraction by adding more water/HF blend to the removed first phase. One may optionally thereafter separate the hydrogen fluoride and water by means well known in the art. For example, one can heat the concentrated HF/water phase at temperatures of up to 150 ° C. to recover HF. The HF may then be recycled to an HFC formation step and preferably, the diluted water/HF blend is also recycled to extract more HF.

The invention can be used for separating a mixture of other halocarbons having fewer than three carbon atoms and hydrogen fluoride. This is done by adding a blend comprising water and hydrogen fluoride to the mixture. A first phase rich in the halocarbon and a second phase rich in hydrogen fluoride and water are formed. The weight ratios of water to hydrogen fluoride and other conditions that are described above can be used to effect the extraction and separation of the phases.

In another exemplary embodiment of the invention, there is used as the extractant water alone, that is, water that is substantially free of HF. The water is typically neutral, that is, it has a pH of about 6 to about 7. When such water is used as the extractant, the amount of water may be that amount effective to remove HF from the mixture of HFC and hydrogen fluoride, and may be used in an excess amount. In this embodiment, the HFC has at least three carbon atoms and preferably three, four or five carbon atoms. The weight ratio of added water to hydrogen fluoride ranges from about 3:2 to about 1:5. More preferably the weight ratio ranges from about 3:2 to about 1:4 and most preferably from about 3:2 to about 1:3. In the preferred embodiment, the separating is conducted at the temperatures mentioned above. Also in the preferred embodiment, the mixture of HFC and hydrogen fluoride and the formed second phase are all azeotropic mixtures. In the preferred embodiment, the weight ratio of water to hydrogen fluoride in the resulting second phase also ranges from about 3:2 to about 1:5, more preferably the weight ratio ranges from about 3:2 to about 1:4 and most preferably from about 3:2 to about 1:3.

After the formation of the separate phases, one removes the phase rich in HFC from the phase rich in hydrogen fluoride and water. The HFC rich phase has, as indicated above, a relatively small amount of HF, that is, no greater than about 1 wt. %, preferably no greater than about 0.5 wt. %, and more preferably no greater than about 0.1 wt. %. Multiple extractions may be used to remove substantially all of the HF from the HFC-containing composition. The phases may be separated from each other by decanting, siphoning, distillation or other techniques well known in the art. As mentioned above, one may optionally repeat the extraction by adding more water or even a water/HF blend to the removed first phase, optionally, one may thereafter separate the hydrogen fluoride and water by means well known in the art. The HF may then be recycled to the HFC formation step and preferably, the diluted water/HF blend may also be recycled to extract more HF. As mentioned above, in connection with the water/HF extraction, "water" extraction can be used also with other halocarbon extraction processes.

EXAMPLES

The following non-limiting examples serve to illustrate the invention.

Example 1

54 g of an azeotropic mixture containing about 71 wt. % HF and about 29 wt. % of HFDC-356 mcfq were contacted with 55 g of an azeotropic blend containing about 42 wt. % HF and about 58 wt. % water and two phases formed immediately. An organic rich phase was formed which was composed of essentially all of the HFC-356 mcfq and only 0.67 wt. % HF and ***** a moisture content of 466 ppm. A second phase contained approximately 67.7 wt. % HF, 0.33 wt. % organics and the balance water. From the material balance, the extraction efficiency is calculated, within experimental error, to be 102%. This experiment was done at room temperature (25° C.). The HF concentration was determined by ion chromatography.

Example 2

78.7 g of an azeotropic mixture containing about 74 wt. % of HFC-245fa and about 26 wt. % of HF is contacted with 69.68 g of an azeotropic blend containing about 37.2 wt. % HF and the balance water and two phases form immediately. An organic rich phase was formed which was composed of essentially all of the HFC-245fa and only 0.1 wt. % HF. A second phase contained approximately 49.7 wt. % HF, and the balance water. From the material balance, the extraction efficiency is calculated, within experimental error, to be 96%. This experiment was done at room temperature (25° C.). The HF concentration was determined by ion chromatography.

Example 3

Binary compositions containing solely HFC-245fa and HF are blended to form a homogeneous azeotrope mixture. The vapor pressures of the mixtures as a function of compositions (wt. % HF) are measured at 20° C. and 75° C. and the following results are noticed.

TABLE 1

| | Pressure (PSIA) | |
| --- | --- | --- |
| Weight Percent HF | T = 20° C. | T = 75° C. |
| 0.0 | 17.6 | 100.3 |
| 8.3 | 25.3 | 138.9 |
| 19.9 | 26.2 | 141.8 |
| 23.1 | 26.3 | 141.6 |
| 32.7 | 26.1 | 138.9 |
| 39.5 | 26.1 | 136.6 |
| 47.9 | 25.8 | 133.3 |
| 100.0 | 14.9 | 81.4 |

The data show that the vapor pressure of mixtures of HFC-245fa and HF is higher, at all indicated blend proportions, than HFC-245fa and HF alone, i.e., as indicated in the first and last rows when HF is 0.0 wt. % and HFC-245fa is at 100.0 wt. %, as well as when HFC-245fa is at 0.0 wt. % and HF is at 100.0 wt. %. The data also show that the azeotropic compositions (the composition at which the pressure is maximum) at 20° C. is about 23.1 wt. % HF (between 19.9 and 32.7 wt. % HF), and at 75° C. is about 19.9 wt. % HF (between 8.3 and 23.1 wt. % HF). The vapor-liquid equilibrium of the mixtures are measured at temperatures of from about 20° C. and 75° C. and the following results are noticed.

TABLE 2

| | | Compositions (Weight Percent HF, ±3%) | |
| --- | --- | --- | --- |
| Temperature ° C. | Pressure (PSIA) | Liquid | Vapor |
| 19.8 | 25.8 | 48.3 | 27.8 |
| 74.6 | 132.8 | 53.0 | 24.5 |
| 19.8 | 26.1 | 32.7 | 27.5 |
| 19.8 | 26.2 | 20.2 | 23.9 |
| 74.6 | 141.8 | 15.9 | 16.2 |

A comparison of the data from Tables 1 and 2 indicates that the vapor-liquid equilibrium results from Table 2 are in agreement the vapor pressure measurements of Table 1.

Example 4

Binary compositions containing solely HFC-356 mcfq and HF are blended to form a homogeneous azeotrope mixture. The vapor pressures of the mixtures as a function of compositions are measured at −0.4° C., 19.8 and 60.1° C. and the following results are noticed.

TABLE 3

| Vapor Pressure Measurement of HFC-356 mcfq/HF | | |
| --- | --- | --- |
| Weight Percent | Pressure (PSIA) | |
| HFC-356 mcfq | T = −0.4° C. | T = 19.8° C. |
| 0.0 | 7.01 | 14.87 |
| 2.09 | 7.04 | 14.91 |
| 5.42 | 7.05 | 15.05 |
| 8.90 | 7.10 | 15.15 |
| 12.46 | 7.11 | 15.26 |
| 16.53 | 7.15 | 15.34 |
| 18.92 | 7.14 | 15.39 |
| 22.24 | 7.18 | 15.47 |
| 30.06 | 7.18 | 15.53 |
| 33.81 | 7.16 | 15.55 |
| 37.19 | 7.13 | 15.53 |

TABLE 4

| Vapor Pressure Measurement of HFC-356 mcfq/HF | | | |
| --- | --- | --- | --- |
| Weight % | Pressure (PSIA) | | |
| HFC-356 mcfq | T = −0.4° C. | T = 19.8° C. | T = 60.1° C. |
| 100.0 | 2.22 | 5.64 | 24.42 |
| 78.54 | 6.33 | 14.40 | 57.18 |
| 68.81 | 6.60 | 14.92 | 58.37 |
| 57.19 | 6.86 | 15.30 | 59.00 |
| 46.60 | 7.00 | 15.52 | 58.89 |
| 38.19 | 7.11 | 15.58 | 58.68 |

TABLE 5

Vapor-Liquid Equilibrium of HFC-356 mcfq/HF

| Temperature (° C.) | Pressure (PSIA) | Wt. % HFC-356 mcfq (±3%) Liquid | Wt. % HFC-356 mcfq (±3%) Vapor | Wt. % HFC-356 mcfq Loaded |
|---|---|---|---|---|
| −0.4 | 7.0 | 41.8 | 41.3 | 37.2 |
| 19.8 | 15.58 | 40.2 | 41.3 | 37.2 |
| −0.4 | 7.0 | 35.2 | 30.6 | 32.6 |
| 19.8 | 15.45 | 33.3 | 35.7 | 32.6 |

The data show that the vapor pressure of mixtures of HFC-356 mcfq and HF is higher, at all indicated blend proportions, than HFC-356 mcfq and HF alone, i.e., as indicated when HF is 0.0 wt. % and HFC-356 mcfq is at 100.0 wt. %, as well as when HFC-356 mcfq is at 0.0 wt. % and HF is at 100.0 wt. %. The data also show that the azeotropic composition (the composition at which the vapor pressure is maximum) is about 40± wt. % HF. The vapor-liquid equilibrium (VLE) of the HFC-356 mcfq/HF mixtures are measured at the temperature of about. 0° C. and 20° C., and the results are reported in Table 5. A comparison of the data from Tables 3, 4 and 5 indicates that the vapor-liquid equilibrium results are in agreement with the vapor pressure measurements.

What is claimed is:

1. A process for separating by extraction a hydrofluorocarbon and hydrogen fluoride from an azeotropic mixture comprising a hydrofluorocarbon containing at least three carbon atoms and at least about 25 wt. % of hydrogen fluoride which comprises adding a blend comprising water and hydrogen fluoride to said azeotropic mixture to thereby form a first phase rich in the hydrofluorocarbon and containing no greater than about 1 wt. % of hydrogen fluoride and a second phase rich in hydrogen fluoride and water, wherein the weight ratio of water to hydrogen fluoride in the added blend ranges from about 2:3 to about 4:1 and wherein the weight ratio of water to hydrogen fluoride in the formed second phase ranges from about 1:3 to about 1:1.

2. The process of claim 1 wherein the czeotropic mixture contains at least about 30 wt. % hydrogen fluoride.

3. The process of claim 1 wherein the first phase contains no greater than about 0.5 wt. % hydrogen fluoride.

4. The process of claim 1 wherein the first phase contains no greater than about 0.1 wt. % hydrogen fluoride.

5. The process of claim 1 wherein the hydrofluorocarbon has four carbon atoms.

6. The process of claim 1 wherein the hydrofluorocarbon has five carbon atoms.

7. The process of claim 1 wherein the hydrofluorocarbon comprises 1,1,1,3,3-pentafluoropropane.

8. The process of claim 1 wherein the hydrofluorocarbon comprises 1,1,2,3,3-pentafluoropropane.

9. The process of claim 1 wherein the hydrofluorocarbon comprises 1,1,1,2,2,5-hexafluorobutane.

10. The process of claim 1 wherein the blend of water and hydrogen fluoride is a binary azeotrope.

11. The process of claim 1 further comprising the subsequent step of removing the first phase rich in the hydrofluorocarbon from the second phase rich in the hydrogen fluoride and water.

12. The process of claim 11 further comprising the subsequent step of separating the hydrogen fluoride and water in the second phase.

13. The process of claim 1 wherein the extraction is conducted at a temperature of from about 0° C. to about 100° C.

14. The process of claim 13 wherein the extraction is conducted at a temperature of about 0° C. to about 40° C.

15. A process for separating by extraction a hydrofluorocarbon and hydrogen fluoride from an azeotropic mixture comprising a hydrofluorocarbon containing at least three carbon atoms and at least about 25 wt. % of hydrogen fluoride which comprises adding neutral water to said azeotropic mixture to thereby form a first phase rich in the hydrofluorocarbon and containing no greater than about 1 wt. % of hydrogen fluoride and a second phase rich in hydrogen fluoride and water, wherein the weight ratio of added water to hydrogen fluoride ranges from about 3:2 to about 1:5 and wherein the weight ratio of water to hydrogen fluoride in the formed second phase ranges from about 3:2 to about 1:5.

16. The process of claim 15 wherein the azeotropic mixture contains at least about 30 wt. % hydrogen fluoride.

17. The process of claim 15 wherein the first phase contains no greater than about 0.5 wt. % hydrogen fluoride.

18. The process of claim 15 wherein the first phase contains no greater than about 0.1 wt. % hydrogen fluoride.

19. The process of claim 15 wherein the hydrofluorocarbon has four carbon atoms.

20. The process of claim 15 wherein the hydrofluorocarbon has five carbon atoms.

* * * * *